May 24, 1966 E. S. BOERNER Plant Pat. 2,636
ROSE PLANT
Filed May 6, 1965
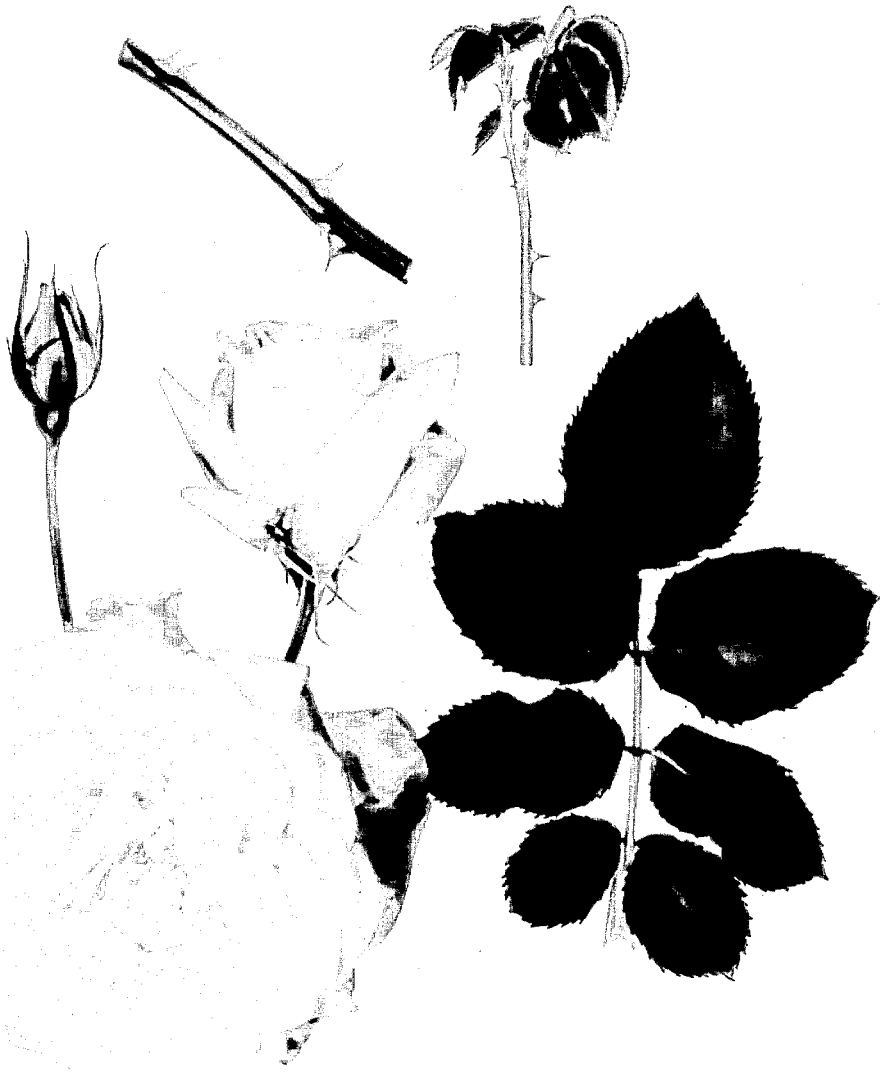
Inventor.
E. S. Boerner
By: Robb & Robb
Attorneys.

United States Patent Office

Plant Pat. 2,636
Patented May 24, 1966

2,636
ROSE PLANT

Eugene S. Boerner, Newark, N.Y., assignor to Jackson & Perkins Company, Newark, N.Y., a corporation of New York Filed May 6, 1965, Ser. No. 453,852
1 Claim. (Cl. Plt.—12)

The present invention relates to a new and distinct variety of rose plant of the hybrid tea class, which was originated by me by crossing the variety "Kordes' Perfecta" (Plant Patent No. 1,604) with an unnamed and unpatented red flowered seedling of unidentified parentage.

The primary objective of this breeding was to produce a new and improved red flowered rose variety generally conforming to the well known parent variety "Kordes' Perfecta." This objective was fully achieved along with other desirable improvements, as evidenced by the following unique combination of characteristics which are outstanding in the new variety and which distinguish it from its parents, as well as from all other varieties of which I am aware:

(1) Exceptionally rich green foliage;

(2) A free blooming habit throughout the season;

(3) A large flower size throughout the blooming season; and (4) An unusual, distinctive and attractive flower color, with the inside of the flower petal corresponding to Rose Red, very lightly overcast with Spectrum Red, and the reverse side of the petals corresponding to Deep Rose Pink over the outer edges of the petals, with the center of the petals corresponding to Marguerite Yellow.

A sexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Kordes' Perfecta."
*Pollen parent.*—An unnamed red flowered seedling of unidentified parentage.

Classification:
*Botanic.*—Hybrid tea.
*Commercial.*—Hybrid tea.

*Flower*

(Observations made from specimens grown outdoors at Newark, New York, in mid-morning during late September.)

Blooming habit: Recurrent—continuous.

Bud:
*Size.*—Medium.
*Form.*—Ovoid; is not affected by wet or hot weather.
*Color.*—When sepals first divide—Oxblood-Red, Plate 1. When petals begin to unfurl—Carmine, Plate 1. When half-blown: Inside of petals—Spectrum Red, Plate 1, very lightly overcast with Carmine, Plate 1; reverse of petals—Spinel Pink, Plate 26, with center of petal Naphthalene Yellow, Plate 16, and lower half of petal lightly overcast with Marguerite Yellow, Plate 30.
*Sepals.*—Slightly branched; curl back when petals begin to unfurl. Color: Inside—Pale Fluorite Green, Plate 32; outside—Lettuce Green, Plate 5.
*Calyx.*—Color—Lettuce Green, Plate 5. Shape—pear. Size—long. Aspect—smooth. Odor when rubbed—none.
*Peduncle.*—Length—medium. Aspect—smooth. Strength—stiff; slender. Color—Biscay Green, Plate 17, lightly overcast with Tawny-Olive, Plate 29.
*Opening.*—Opens up well; is not affected by adverse weather conditions.

Bloom:
*Size.*—Large. Average size when fully expanded—from 5 inches to 5½ inches.
*Borne.*—Both singly and several together.
*Stems.*—Long; strong.
*Form (when first open).*—High-centered. Permanence—retains its form to the end.
*Petalage.*—Double (full but open center). Number of petals under normal conditions—from 30 to 35.
*Color.*—Center of flower—Rose Red, Plate 12, lightly overcast with Spectrum Red, Plate 1. Outer petals—Rose Red, Plate 12, with outer edge of petals very lightly overcast with Carmine, Plate 1. Base of petals (aiglet)—Chartreuse Yellow, Plate 31. Inside of petals—Rose Red, Plate 12, very lightly overcast with Spectrum Red, Plate 1. Reverse of petals—Deep Rose Pink, Plate 12 about outer edge of petal, with center of petal Marguerite Yellow, Plate 30 and lightly overcast with Marguerite Yellow, Plate 30 toward the base of the petal. General tonality from a distance—Rose Red, Plate 12, very lightly overcast with Spectrum Red, Plate 1.
*Discloration.*—General tonality at end of first day—Rose Red, Plate 12, very lightly overcast with Spectrum Red, Plate 1. Second day—Rose Red, Plate 12, very lightly overcast with Spectrum Red, Plate 1. Third day—Rose Red, Plate 12.

Petals:
*Texture.*—Leathery; is not affected by wet or hot weather.
*Appearance.*—Inside—velvety. Outside—satiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Antimony Yellow, Plate 15.
Stamens, filaments (threads): Medium length. Color—Picric Yellow, Plate 4.
Pollen: Color—Light Buff, Plate 15.
Styles: Bunched; uneven length; medium; thin.
Stigmas: Color—Partridge Buff, Plate 30.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Normal.
*Color.*—New foliage: Upper side—Garnet Brown, Plate 1; under side—Yellowish-Oil Green, Plate 5, overcast with Van Dyke Red, Plate 13. Old foliage: Upper side—Dark Cress Green, Plate 31; under side—Light Cress Green, Plate 31.
*Shape.*—Oval pointed.
*Texture.*—Upper side—leathery and glossy. Under side—smooth.
*Ribs and veins.*—Ordinary.
*Edge.*—Serrated (saw toothed).
*Serration.*—Both double and single; large.
*Leaf stem.*—Color—Mignonette Green, Plate 31, overcast lightly with Van Dyke Red, Plate 13. Under side—prickly.
*Stipules.*—Medium length; smooth.
Wood:
*New wood.*—Color—Neutral Red, Plate 38. Bark—rough.
*Old wood.*—Color—Cress Green, Plate 31. Bark—rough.

Thorns:
*Thorns.*—Quantity: On main stalks from base—ordinary; on laterals from stalks—ordinary. Form—narrow base; medium length; hooked downward. Color (when young)—Oxblood Red, Plate 1. Position—irregular.
*Prickles.*—Quantity: On main stalks—none; on laterals—none.
*Short needles.*—Quantity: On main stalks—none; on laterals—none.

I claim:

A new and distinct variety of rose plant of the hybrid tea class, substantially as herein shown and described, characterized particularly as to novelty by the unique combination of exceptionally rich green foliage, a free blooming habit throughout the season, a large flower size throughout the blooming season, and an unusual, distinctive and attractive flower color, with the inside of the flower petals corresponding to Rose Red, very lightly overcast with Spectrum Red, and the reverse of the petals corresponding to Deep Rose Pink over the outer edges of the petals, with the center fo the petals corresponding to Marguerite Yellow.

No references cited.

ABRAHAM G. STONE, *Primary Examiner.*